(12) United States Patent
Modak et al.

(10) Patent No.: US 6,224,579 B1
(45) Date of Patent: May 1, 2001

(54) TRICLOSAN AND SILVER COMPOUND CONTAINING MEDICAL DEVICES

(75) Inventors: Shanta Modak, River Edge, NJ (US); Lester Sampath, Nyack, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/281,872

(22) Filed: Mar. 31, 1999

(51) Int. Cl.$^7$ ............................................. A61M 5/32
(52) U.S. Cl. ............................ 604/265; 424/422; 623/1; 428/35.7
(58) Field of Search .................... 604/265, 264; 428/35.7, 36.9; 606/76; 424/422; 623/1

(56) References Cited

U.S. PATENT DOCUMENTS

| | | |
|---|---|---|
| 4,605,564 | 8/1986 | Kulla et al. . |
| 4,723,950 | 2/1988 | Lee . |
| 4,994,047 | 2/1991 | Walker et al. . |
| 5,019,096 | 5/1991 | Fox, Jr. et al. . |
| 5,033,488 | 7/1991 | Curtis et al. . |
| 5,091,442 | 2/1992 | Milner . |
| 5,102,401 | 4/1992 | Lambert et al. . |
| 5,165,952 | 11/1992 | Solomon et al. . |
| 5,180,605 | 1/1993 | Milner . |
| 5,200,194 | 4/1993 | Edgren et al. . |
| 5,209,251 | 5/1993 | Curtis et al. . |
| 5,261,421 | 11/1993 | Milner . |
| 5,335,373 | 8/1994 | Dangman et al. . |
| 5,357,636 | 10/1994 | Dresdner et al. . |
| 5,772,640 | * 6/1998 | Modak et al. ...................... 604/265 |

FOREIGN PATENT DOCUMENTS 9302717  2/1993  (WO) .

OTHER PUBLICATIONS

The Merck Index, An Encyclopedia of Chemicals, Drugs and Biologicals, Tenth Edition (Merck & Co., Inc., Rahway, NJ, 1983), p. 1092.

* cited by examiner

*Primary Examiner*—Sharon Kennedy
(74) *Attorney, Agent, or Firm*—Baker Botts L.L.P.

(57) ABSTRACT

The present invention relates to polymeric medical articles comprising combinations of triclosan and silver-containing compounds. It is based, at least in part, on the discovery that these agents act synergistically, thereby permitting the use of relatively low levels of both agents. While it had been previously found that triclosan can be particularly useful when used in conjunction with chlorhexidine, it has been further discovered that medical articles having suitable antimicrobial properties may be prepared, according to the present invention, which contain triclosan without chlorhexidine. Such medical articles offer the advantage of preventing or inhibiting infection while avoiding undesirable adverse reactions to chlorhexidine by individuals that may have sensitivity to chlorhexidine.

20 Claims, No Drawings

TRICLOSAN AND SILVER COMPOUND CONTAINING MEDICAL DEVICES

1.0 INTRODUCTION

The present invention relates to medical devices comprising synergistic combinations of triclosan and silver containing compounds.

2.0 BACKGROUND OF THE INVENTION

Whenever a medical device comes in contact with a patient, a risk of infection is created. Thus, a contaminated examination glove, tongue depressor, or stethoscope could transmit infection. The risk of infection dramatically increases for invasive medical devices, such as intravenous catheters, arterial grafts, intrathecal or intracerebral shunts and prosthetic devices, which not only are, themselves, in intimate contact with body tissues and fluids, but also create a portal of entry for pathogens.

A number of methods for reducing the risk of infection have been developed which incorporate anti-infective agents into medical devices, none of which have been clinically proven to be completely satisfactory. Such devices desirably provide effective levels of anti-infective agent during the entire period that the device is being used. This sustained release may be problematic to achieve, in that a mechanism for dispersing anti-infective agent over a prolonged period of time may be required, and the incorporation of sufficient amounts of anti-infective agent may adversely affect the surface characteristics of the device. The difficulties encountered in providing effective antimicrobial protection increase with the development of drug-resistant pathogens.

One potential solution to these problems is the use of a synergistic combination of anti-infective agents that requires relatively low concentrations of individual anti-infective agents which may have differing patterns of bioavailability.

Two well-known anti-infective agents are chlorhexidine and triclosan. The following patents and patent application relate to the use of chliorhexidine and/or triclosan in medical devices.

U.S. Pat. No. 4,723,950 by Lee relates to a microbicidal tube which may be incorporated into the outlet tube of a urine drainage bag. The microbicidal tube is manufactured from polymeric materials capable of absorbing and releasing anti-microbial substances in a controllable sustained time release mechanism, activated upon contact with droplets of urine, thereby preventing the retrograde migration of infectious organisms into the drainage bag. The microbicidal tube may be produced by one of three processes: (1) a porous material, such as polypropylene, is impregnated with at least one microbicidal agent, and then coated with a hydrophilic polymer which swells upon contact with urine, causing the leaching out of the microbicidal agent; (2) a porous material, such as high density polyethylene, is impregnated with a hydrophilic polymer and at least one microbicidal agent; and (3) a polymer, such as silicone, is compounded and co-extruded with at least one microbicidal agent, and then coated with a hydrophilic polymer. A broad range of microbicidal agents are disclosed, including chlorhexidine and triclosan, and combinations thereof. The purpose of Lee's device is to allow the leaching out of microbicidal agents into urine contained in the drainage bag; similar leaching of microbicidal agents into the bloodstream of a patient may be undesirable.

U.S. Pat. No. 5,091,442 by Milner relates to tubular articles, such as condoms and catheters, which are rendered antimicrobially effective by the incorporation of a non-ionic sparingly soluble antimicrobial agent, such as triclosan. The tubular articles are made of materials which include natural rubber, polyvinyl chloride and polyurethane. Antimicrobial agent may be distributed throughout the article, or in a coating thereon. A condom prepared from natural rubber latex containing 1% by weight of triclosan, then dipped in an aqueous solution of chlorhexidine, is disclosed. U.S. Pat. Nos. 5,180,605 and 5,261,421, both by Milner, relate to similar technology applied to gloves.

U.S. Pat. Nos. 5,033,488 and 5,209,251, both by Curtis et al., relate to dental floss prepared from expanded polytetrafluoroethylene (PTFE) and coated with microcrystalline wax. Antimicrobial agents such as chlorhexidine or triclosan may be incorporated into the coated floss.

U.S. Pat. No. 5,200,194 by Edgren et al. relates to an oral osmotic device comprising a thin semipermeable membrane wall surrounding a compartment housing a "beneficial agent" (that is at least somewhat soluble in saliva) and a fibrous support material composed of hydrophilic water-insoluble fibers. The patent lists a wide variety of "beneficial agents" which may be incorporated into the oral osmotic device, including chlorhexidine and triclosan.

U.S. Pat. No. 5,019,096 by Fox, Jr., et al. relates to infection-resistant medical devices comprising a synergistic combination of a silver compound (such as silver sulfadiazine) and chlorhexidine.

International Patent Application No. PCT/GB92/01481, Publication No. WO 93/02717, relates to an adhesive product comprising residues of a copolymerisable emulsifier comprising a medicament, which may be povidone iodine, triclosan, or chlorhexidine.

International Patent Application No. PCT/US96/20932, Publication No. WO 97/25085, relates to polymeric medical articles comprising synergistic combinations of chlorhexidine and triclosan which utilize relatively low levels of these agents.

In contrast to the present invention, none of the above-cited references teach medical articles comprising synergistic combinations of triclosan and silver compounds which utilize relatively low levels of these agents and provide effective levels of antimicrobial activity, even in the absence of chlorhexidine.

3.0 SUMMARY OF THE INVENTION

The present invention relates to polymeric medical articles comprising combinations of triclosan and/or other chlorinated phenols and silver-containing compounds. It is based, at least in part, on the discovery that these agents act synergistically, thereby permitting the use of relatively low levels of both agents. While it had been previously found that triclosan can be particularly useful when used in conjunction with chlorhexidine, it has been further discovered that medical articles having suitable antimicrobial properties may be prepared, according to the present invention, which contain triclosan and a silver compound without chlorhexidine. Such medical articles offer the advantage of preventing or inhibiting infection while avoiding undesirable adverse reactions to chlorhexidine by individuals that may have a sensitivity to chlorhexidine, such as a chlorhexidine allergy.

The present invention is also based, at least in part, on the discovery that the surface of medical articles, especially catheters, impregnated with triclosan and silver compounds generally were found to be smoother and shinier in comparison with catheters impregnated with triclosan and chlorhexidine. Even when the triclosan-silver compound impregnated catheters exhibited commensurate or smaller zones of inhibition compared to triclosan-chlorhexidine catheters, there was little or no bacterial adherence observed on the former when exposed to bacterial culture. Microbial adherence on the surfaces of medical devices are the result of a deposition of fibrinogen and fibronectin on the surface which forms a host biofilm. Because bacteria tend to adhere to this biofilm, glycocalyx forms which serves as a bacterial reservoir causing blood stream infections. Without being bound by any particular theory, it is believed that medical articles of the invention, by virtue of their smooth surfaces, may be less physically irritating than prior art devices, may be less likely to provoke fibrinogen and/or fibronectin deposition, and therefore may avoid bacterial colonization.

4.0 DETAILED DESCRIPTION OF THE INVENTION

The present invention relates to medical articles comprising combinations of triclosan and/or another chlorinated phenol and one or more silver-containing compound (hereafter, "silver compound").

While not being bound or limited by any particular theory, it is believed that the combination of triclosan and a silver compound forms a soluble complex. This would explain observations, such as those set forth in Example Section 5 below, that the presence of triclosan improves the solubility of various silver compounds, thereby improving their bioavailability.

As shown in Example Sections 7, 9–17 and 19, medical articles, which may be hydrophilic or hydrophobic, treated with combinations of triclosan and various silver compounds exhibit desirable antimicrobial properties. As shown in Example Sections 8, 13 and 14 such articles exhibit smooth surfaces that tend to resist bacterial adherence, which may be at least partly responsible for their antimicrobial quality.

The present invention provides for medical articles treated with chlorinated phenols other than triclosan in combination with one or more silver compound. As shown in Example Section 18, such combinations result in enhanced antimicrobial activity. Suitable chlorinated phenols include parachlorometaxylenol ("PCMX") and dichlorometaxylenol ("DCMX"). The amount of chlorinated phenol which may be used is as set forth below for triclosan, but may be adjusted for differences in potency when tested against a particular microbe. For example, in specific, non-limiting embodiments of the invention polymeric medical articles may be prepared using treatment solutions comprising between about 0.1 and 5 percent, preferably between about 0.3 and 1.5 percent, of a silver compound, and between about 0.1 and 20 percent, preferably between about 0.1 and 8 percent, of a chlorinated phenol, preferably PCMX. The present invention also provides for medical articles comprising triclosan in addition to another chlorinated phenol.

In additional embodiments, the present invention provides for medical articles having anti-infective activity which comprise triclosan and/or another chlorinated phenol, a silver compound, and an anti-inflammatory agent. It has been found that the addition of an anti-inflammatory compound enhances the antimicrobial activity of such devices (see Section 17 below).

In still further embodiments, the present invention provides for medical articles which have been treated with a hydrogel, and further comprise a metal compound.

The term triclosan ("TC"), as used herein, refers to a compound also known as 2,4,4'-trichloro-2'-hydroxydiphenyl ether and also known as 5-chloro-2-(2,4-dichlorophenoxy)phenol.

The term silver compound, as used herein, refers to a compound comprising silver, either in the form of a silver atom or a silver ion unlinked or linked to another molecule via a covalent or noncovalent (e.g., ionic) linkage, including but not limited to covalent compounds such as silver sulfadiazine ("AgSD") and silver salts such as silver oxide ("$Ag_2O$"), silver carbonate ("$Ag_2CO_3$"), silver deoxycholate, silver salicylate, silver iodide, silver nitrate ("$AgNO_3$"), silver paraaminobenzoate, silver paraaminosalicylate, silver acetylsalicylate, silver ethylenediaminetetraacetic acid ("Ag EDTA"), silver picrate, silver protein, silver citrate, silver lactate and silver laurate.

The terms "medical article" and "medical device" are used interchangeably herein. Medical articles that may be treated according to the invention are either fabricated from or coated or treated with biomedical polymer (and hence may be referred to as "polymer-containing medical articles") and include, but are not limited to, catheters including urinary catheters and vascular catheters (e.g., peripheral and central vascular catheters), wound drainage tubes, arterial grafts, soft tissue patches (such as polytetrafluoroethylene ("PTFE") soft tissue patches), gloves, shunts, stents, tracheal catheters, wound dressings, sutures, guide wires and prosthetic devices (e.g., heart valves and LVADs). Vascular catheters which may be prepared according to the present invention include, but are not limited to, single and multiple lumen central venous catheters, peripherally inserted central venous catheters, emergency infusion catheters, percutaneous sheath introducer systems and thermodilution catheters, including the hubs and ports of such vascular catheters. The present invention may be further applied to medical articles that have been prepared according to U.S. Pat. No. 5,019,096 by Fox, Jr. et al.

The following are descriptions of particular embodiments of the invention.

Percentages recited herein refer to weight/volume (w/v), except as indicated otherwise.

The present invention provides, in various non-limiting embodiments, for: (1) treatment solutions comprising between about 0.1 and 5 percent, and preferably between about 0.3 and 1.5 percent of a silver compound; and between about 0.1 and 20 percent and preferably between about 0.1 and 8 percent of triclosan and/or other chlorinated phenol; (2) treatment solutions comprising between about 0.1 and 10 percent, and preferably between about 1 and 5 percent of one or more hydrophilic or hydrophobic polymer; between about 0.1 and 5 percent, and preferably between about 0.3 and 1.5 percent of a silver compound; and between about 0.1 and 20 percent, and preferably between about 0.1 and 8 percent of triclosan and/or other chlorinated phenol; (3) polymer-containing medical articles treated with a treatment solution as set forth in (1) or (2) above, and articles physically equivalent thereto (that is to say, articles prepared by a different method but having essentially the same elements in the same proportions); (4) polymer-containing medical articles treated with treatment solutions set forth in (1) or (2) above wherein the articles are dried and thereafter coated with an anti-infective and/or polymeric coating in accordance with a two-step process. The treatment solutions set forth in (1) or (2) may optionally further comprise (i) an organic acid, at a concentration of between about 0.1 and 5 percent, preferably between about 0.1 and 2 percent; (ii) an anti-inflammatory agent, at a concentration of between about 1 and 5 percent, preferably between about 0.1 and 1 percent; (iii) an antimicrobial other than a silver compound or triclosan at a concentration of between about 0.1 and 10 percent; and/or (iv) a hydrogel at a concentration of between about 0.5 to 10 percent, preferably between about 1 and 5 percent. In preferred non-limiting embodiments of the invention, the amount of silver present as silver atom or silver ion is about 0.9%. In preferred non-limiting embodiments of the invention, the treatment solution and/or medical article does not contain chlorhexidine or a chlorhexidine salt. The medical articles are "treated" by exposing them, for an effective period of time, to the treatment solution, where an "effective period of time" is that period of time sufficient to introduce anti-infective quantities of triclosan and/or other chlorinated phenol and silver compound. Where the concentration of gtriclosan and/or other chlorinated phenol in the treatment solution is between 0.1 and 8 percent, the effective period of time may be between about 30 seconds and one hour; where the concentration of tricolsan and/or other chlorinated phenol in the treatment solution is between about 9 and 20 percent, the effective period of time may be between about 10 seconds and 2 minutes. Longer periods of exposure may be used provided that undesirable deterioration of the medical article does not occur.

The term "about" indicates a variation within 20 percent.

In particular non-limiting embodiments of the invention, where the medical article is a vascular catheter, such as a central venous catheter, the amount of triclosan contained is about 100–600 $\mu$g/cm, preferably about 400–500 $\mu$g/cm and the amount of silver atom or ion is 25 to 100 $\mu$g/cm, preferably 30 to 80 $\mu$g/cm. The triclosan and silver are in releasable form, i.e., extractable by a solvent that does not substantially dissolve the catheter.

Medical articles prepared according to the invention may be treated on their external surface, internal surface, or both. For example, and not by way of limitation, where the medical article is a catheter, the internal surface and/or external surface of the catheter may be treated according to the invention. For example, where it is desired to treat both internal and external surfaces, an open-ended catheter may be placed in a treatment solution such that the treatment solution fills the catheter lumen. If only the external surface is to come in contact with treatment solution, the ends of the catheter may be sealed before it is placed in the treatment solution. If only the internal surface is to come in contact with treatment solution, the solution may be allowed to pass through and fill the lumen but the catheter is not immersed in the treatment solution.

Medical articles may be dipped, soaked, or otherwise have a surface coated. The term "dipped" suggests briefer exposure to treatment solution relative to soaking, and preferably is for a period of time less than fifteen minutes.

Successftil treatment of a medical article with a polymer comprising an anti-infective agent may be problematic, particularly where the medical article has a hydrophobic surface. The adherence of the polymer may depend upon (1) the polymeric matrix in which the anti-infective agent is suspended; (2) compatibility (or lack thereof) between the agent-polymcric matrix and the surface of the article; (3) the solvent system; and (4) the thickness of polymer/anti-infective agent desirably applied. Furthermore, the rates of release of various anti-infective agents from diverse polymers may differ. To address these issues, the present invention provides for two different methods for treating medical articles: a one-step method, and a two-step method, both of which are set forth below.

Polymers, triclosan, and silver compounds used according to the invention may be sparingly soluble in certain solvents or solvent mixtures. It therefore may be desirable to first dissolve the relevant material in a solvent or component of a solvent system which favors dissolving. For example, where polyurethane, triclosan, and a silver compound are desirably incorporated into an alcohol/tetrahydrofuran ("THF") solvent system, the polyurethane may first be dissolved in THF and the triclosan and silver compound may be dissolved in alcohol (in certain instances with the addition of an aqueous solution of ammonia (referred to interchangeably herein as either ammonia, ammonium hydroxide, or $NH_3$) to facilitate solubilization of the silver compound), before the THF and alcohol components are mixed. The use of a solvent system comprising ammonia may be particularly desirable when a silver salt is used.

4.1 HYDROPHILIC ARTICLE TREATED WITH A SOLUTION OF A HYRDOPHILIC POLYMER

In one particular set of non-limiting embodiments, the present invention provides for a hydrophilic polymeric medical article (i.e., a medical article fabricated from a hydrophilic polymer) treated by coating, dipping or soaking the article in a treatment solution of a hydrophilic polymer comprising a silver compound and triclosan (and/or other chlorinated phenol) wherein the silver compound and triclosan or other chlorinated phenol are present in amounts such that their combination, in the treated article, has effective anti-microbial activity. The term "effective antimicrobial activity" refers to an ability to decrease the number of colony-forming units of a bacterium or yeast, in a 24 hour period, by a factor of ten or more and preferably a factor of 100 or more. The terms "treat", "treated", etc., as used herein, refer to coating, impregnating, or coating and impregnating a medical article with anti-infective agent. The term "hydrophilic polymer", as used herein, refers to polymers which have a water absorption greater than 0.6 percent by weight (and, in preferred embodiments, less than 2 percent by weight; as measured by a 24 hour immersion in distilled water, as described in ASTM Designation D570-81) including, but not limited to biomedical polyurethanes (e.g., ether-based polyurethanes and ester-based polyurethanes, as set forth in Baker, 1987, in *Controlled Release of Biologically Active Agents*, John Wiley and Sons, pp. 175–177 and Lelah and Cooper, 1986, *Polyurethianes in Medicine*, CRC Press, Inc., Fla. pp. 57–67; polyurethanes comprising substantially aliphatic backbones such as Tecoflex™ 93A; polytirethanes comprising substantially aromatic backbones such as Tecothane™; and Pellethane™), polylactic acid, polyglycolic acid, natural rubber latex, and gauze or water-absorbent fabric, including cotton gauze and silk suture material. In specific, non-limiting embodiments, the hydrophilic medical article is a polyurethane catheter which has been treated with (e.g., coated, dipped or soaked in) a treatment solution comprising (i) between about 0.1 and 10 percent, and preferably between about 1 and 5 percent, of one or more biomedical polyurethane; (ii) between about 0.1 and 5 percent, and preferably between 0.3 and 1.5 percent, of a silver compound; and (iii) between about 0.1 and 20 percent, and preferably between about 0.1 and 8 percent, of triclosan and/or other chlorinated phenol.

4.2. HYDROPHILIC ARTICLE TREATED WITH A SOLUTION OF A HYDROPHOBIC POLYMER

In another set of particular non-limiting embodiments, the present invention provides for a hydrophilic polymeric medical article treated by coating, dipping or soaking the article in a treatment solution of a hydrophobic polymer comprising a silver compound and triclosan (and/or other chlorinated phenol), wherein the silver compound and triclosan and/or other chlorinated phenol are present in amounts such that their combination, in the treated article, has effective anti-microbial activity. The term "hydrophobic polymer", as used herein, refers to a polymer which has a water absorption of less than 0.6% and includes, but is not limited to, silicone polymers such as biomedical silicones (e.g., Silastic Type A) or elastomers (e.g., as set forth in Baker, 1987, in *Controlled Release of Biologically Active Agents*, John Wiley and Sons, pp. 156–162), Dacron, polytetrafluoroethylene ("PTFE", also "Teflon"), polyvinyl chloride ("PVC"), cellulose acetate, polycarbonate, and copolymers such as silicone-polyurethane copolymers (e.g., PTUE 203 and PTUE 205 polyurethane-silicone interpenetrating polymer). In one specific, non-limiting embodiment, the medical article is a polyurethane catheter which has been dipped or soaked in a treatment solution comprising (i) between about 0.1 and 10 percent, and preferably between about 1 and 5 percent, of a polyurethane-silicone copolymer; (ii) between about 0.1 and 5 percent, and preferably between about 0.3 and 1.5 percent, of a silver compound; and (iii) between about 0.1 and 20 percent, and preferably between about 0.1 and 8 percent, of triclosan and/or other chlorinated phenol.

4.3 HYDROPHOBIC ARTICLE TREATED WITH A SOLUTION OF A HYDROPHOBIC POLYMER

In another set of particular non-limiting embodiments, the present invention provides for a hydrophobic polymeric medical article treated by coating, dipping or soaking the article in a treatment solution of hydrophobic polymer comprising a silver compound and triclosan and/or other chlorinated phenol, wherein the silver compound and triclosan and/or other chlorinated phenol are present in amounts such that their combination, in the treated article, has effective antimicrobial activity. In one specific, non-limiting embodiment, the medical article is a silicone catheter or a polyvinylcbloride catheter which has been dipped or soaked in a treatment solution comprising (i) between about 0.1 and 10 percent, and preferably between about 1 and 5 percent, of a silicone polymer; (ii) between about 0.1 and 5 percent, and preferably between about 0.3 and 1.5 percent, of a silver compound; and (iii) between about 0.1 and 20 percent, and preferably between about 0.1 and 8 percent, of triclosan and/or other chlorinated phenol.

4.4 HYDROPHOBIC ARTICLE TREATED WITH A SOLUTION OF A HYDROPHILIC POLYMER

In yet another set of particular non-limiting embodiments, the present invention provides for a hydrophobic polymeric medical article treated by coating, dipping or soaking the article in a treatment solution of hydrophilic polymer comprising a silver compound and triclosan and/or other chlorinated phenol, wherein the silver compound and triclosan and/or other chlorinated phenol are present in amounts such that their combination, in the treated article, has effective anti-microbial activity. In a specific, non-limiting embodiment, the medical article is a silicone catheter or Teflon graft which has been dipped, coated or soaked in a treatment solution comprising (i) between about 0.1 and 10 percent, and preferably between about 1 and 5 percent, of a biomedical polyurethane polymer; (ii) between about 0.1 and 5 percent, and preferably between about 0.3 and 1.5 percent, of a silver compound; and (iii) between about 0.1 and 20 percent, and preferably between about 0.1 and 8 percent, of triclosan and/or other chlorinated phenol.

4.5 MEDICAL ARTICLES IMPREGNATED WITH TRICLOSAN AND A SILVER COMPOUND BY A ONE-STEP METHOD

According to the one-step method of the invention, a polymeric medical article may be treated with a solution comprising one or more silver compounds, triclosan and/or other chlorinated phenol, and optionally containing a biomedical polymer, dissolved in one or more solvents, wherein the solvent(s) selected is (are) capable of swelling the polymeric medical article to be treated; such a solution is referred to herein as an "impregnating solution" (which is a species of treatment solution), and the process by which the article is treated with triclosan and a silver compound is referred to as "impregnation". Suitable solvents include, but are not limited to, tetrahydrofuran ("THF"), dichloromethane, carbon tetrachloride, methanol, ethanol, methyl ethyl ketone, heptane, M-Pyrol and hexane, and mixtures thereof. The term "reagent alcohol" as used herein refers to a solution containing essentially 5% v/v methanol, 5% v/v isopropanol, and 90% v/v ethanol. The biomedical polymer may be hydrophilic or hydrophobic, and includes the various polymers set forth above.

If a hydrophilic polymeric medical article is to be impregnated with a silver compound and triclosan and/or other chlorinated phenol, the impregnating solution may, in specific non-limiting embodiments, comprise the following (percentages of solvents in this paragraph being volume/volume (v/v) except where noted to be weight/volume (w/v)): 95% ethanol/5% water; 95% reagent alcohol/5% water; 70% ethanol/30% water; 70% reagent alcohol/30% water; 50% ethanol/50% water; 50% reagent alcohol/50% water; 30% ethanol/70% THF; 30% reagent alcohol/70% THF; 30% methanol/70% THF; 10% ethanol/10% ammonia/80% THF; 10% reagent alcohol/10% ammonia/80% THF; 90% ethanol/10% THF; 90% reagent alcohol/10% THF; 90% methanol/10% THF; 100% ethanol or 100% reagent alcohol. The treatment solutions may comprise between about 0.1 and 10 percent (w/v), and preferably between about 1 and 5 percent (w/v), of one or more dissolved polymer (e.g. one or more species of polyurethane, silicone, or hydrogel). Preferred soaking times according to the one-step method vary between 15 seconds and 1 hour, depending upon the polymer selected. A shorter soaking time in a drug/solvent system is preferred since it is less likely to negatively affect the physical integrity of the polymeric device, particularly polyurethane catheters. In order to attain a sufficient drug uptake using a shorter soaking time, it is preferred that the amount of triclosan or other chlorinated phenol in the treatment solution be between about 10 and 20 percent (w/v). For a specific example of a method that uses higher levels of triclosan and a shorter soaking time see Section 9 below.

If a hydrophobic polymeric medical article is to be impregnated with a silver compound and triclosan and/or other chlorinated phenol, the impregnating solution may, in specific non-limiting embodiments, comprise the following (percentages of solvents in this paragraph being volume/volume (v/v) except where noted to be weight/volume (w/v)): 10% methanol/90% THF; 10% ethanol/90% THF; 10% reagent alcohol/90% THF; 10% ethanol/10% ammonia/80% THF; 10% reagent alcohol/10% ammonia/80% THF; 30% ethanol/70% THF; 30% reagent alcohol/70% THF; 30% methanol/70% THF; 1–5 percent (w/v) silicone polymer in 10% methanol/90% THF; 1–5 percent (w/v) silicone polymer in 10% ethanol/90% THF; 1–5 percent (w/v) silicone polymer in 10% reagent alcohol/90% THF; 1–2 percent (w/v) polylactic acid in 10% methanol/90% THF; 1–2 percent w/v polylactic acid in 10% ethanol/90% THF; 1–2 percent (w/v) polylactic acid in 10% reagent alcohol/90% THF; 1–5 percent (w/v) silicone polymer in 30% methanol/70% THF; 1–5 percent (w/v) silicone polymer in 30% ethanol/70% THF; 1–5 percent (w/v) silicone polymer in 30% reagent alcohol/70% THF; 1–2 percent (w/v) polylactic acid in 30% methanol/70% THF; 1–2 percent (w/v) polylactic acid in 30% ethanol/70% THF; 1–2 percent (w/v) polylactic acid in 30% reagent alcohol/70% THF; 1–5 percent (w/v) silicone polymer in 100% methyl ethyl ketone; and 1–2 percent (w/v) polyurethane in 30% ethanol/70% THF. In general, such treatment solutions may comprise between 0.1 and 10 percent, and preferably between about 1 and 5 percent, of one or more dissolved polymer. For specific examples, see Sections 11–12, below, and Section 10, which shows examples of hydrophilic medical articles (e.g., latex urinary catheters) or hydrophobic medical articles (e.g., PTFE soft tissue hernia graft patches) impregnated with triclosan and silver using a solution without polymer.

The medical article, or a portion thereof, may be immersed in the impregnating solution to swell, after which the article may be removed and dried at room temperature until all solvent has evaporated and the article is no longer swollen. Other methods may also be used, such that a substantially uniform coat of impregnating solution is applied. During the swelling process, triclosan or other chlorinated phenol and silver compound (and small amounts of polymer when present in the impregnating solution) may be distributed within the polymeric substrate of the article; during drying, the triclosan or other chlorinated phenol and silver compound and biomedical polymer (where present) may migrate somewhat toward the surface of the article. In the case of PTFE devices, no apparent swelling occurs, however, the drugs are trapped in the interstices of the substrate. After drying, the article may be rinsed in either water or alcohol and wiped to remove any excess triclosan or other chlorinated phenol, silver compound, and/or polymer at the surface. This may leave a sufficient amount of triclosan or other chlorinated phenol and silver compound just below the surface of the article, thereby permitting sustained release over a prolonged period of time.

4.6 TWO-STEP METHOD OF PREPARING ANTI-INFECTIVE MEDICAL ARTICLES

According to the two-step method of the invention, the one-step method may be used to impregnate a medical article with trielosan and/or other chlorinated phenol and a silver compound, and then the medical article may be dipped into a second treatment solution containing triclosan and/or other chlorinated phenol and/or a silver compound and/or one or more polymer, and dried. This method forms a coating on the article and further controls the rate of release of triclosan or other chlorinated phenol and silver compound. For a non-limiting specific example, see Section 7, below.

4.7 MEDICAL ARTICLES HAVING ANTI-ADHERENT PROPERTIES

It has been discovered that medical articles treated with mixtures of silver compounds and triclosan exhibit anti-adherent qualities and anti-microbial effectiveness, even in the absence of chlorhexidine. While not being bound to any particular theory, it is believed that triclosan and silver compounds form a triclosan-silver compound complex, such that impregnation of this triclosan-silver compound complex into medical articles increases resistance to microbial adherence to the surfaces by rendering the surfaces smooth and shiny. It has further been discovered that the combination of silver compounds and other compositions, such as other chlorinated phenolic compounds, anti-inflammatory agents, hydrophilic and hydrophobic polymers and hydrogels each separately contribute to enhanced and prolonged antimicrobial efficacy of the antimicrobial agents. The synergistic combinations of triclosan and silver compounds that are sparingly soluble are especially suitable for forming a smooth surface and for providing a sustained and prolonged release of anti-microbial agents.

In a specific example of a method of direct impregnation of triclosan and a silver compound into a Dacron device, a treatment solution may be prepared including 1 to 6 percent triclosan and 0.1 to 0.2 percent of a silver compound in a solvent mixture containing (v/v) 10 percent ammonia, 10 percent alcohol and 80 percent THF. The device may be soaked for 1 to 10 minutes, dried and rinsed. In variations of this example, between about 1 and 10 percent of a hydrophilic polymer or a hydrophobic polymer may be included in the treatment solution. Suitable hydrophilic polymers include, but are not limited to, one or more of polyurethane, polycaprolactone, and polyactic acid. Suitable hydrophobic polymers include, but are not limited to, silicone polymers.

4.8 MEDICAL ARTICLES COMPRISING TRICLOSAN, A SILVER COMPOUND, AND AN ANTI-INFLAMMATORY AGENT

Anti-inflammatory agents such as salicylic acid, paraaminosalicylic acid, and acetylsalicylic acid were impregnated along with triclosan and a silver compound into medical devices to reduce inflammatory reaction around the wound at the insertion site and thus enhance wound healing. Surprisingly, it has been discovered that incorporation of these anti-inflammatory agents along with the triclosan and a silver compound enhances the anti-microbial activity of the composition. Since the anti-inflammatory agents do not give zones of inhibition when used alone, it appears that increased zone sizes, observed when the anti-inflammatory agents are added to the triclosan and silver compound combination, is not a result of an additive effect but rather due to potentiation of the activity of the complex. Thus, the present invention provides for medical articles treated with treatment solutions comprising triclosan and/or other chlorinated phenol, a silver compound, and an anti-inflammatory agent, such as salicylic acid or a derivative thereof. In further non-limiting embodiments, the treatment solution may also include an additional anti-infective agent such as those set forth below, or chlorhexidine, or a chlorhexidine salt (at a concentration of between about 0.1 and 5 percent).

4.9 ADDITION OF OTHER ANTI-INFECTIVE AGENTS

Because a major route of entry of pathogens during implantation of medical devices occurs at the insertion site and occurs at the time of implantation, it is important to have an effective broad spectrum antimicrobial field around the device during implantation. In order to enhance the antimicrobial field around a device, antibiotic and anti-microbial agents may be added to medical articles comprising triclosan or other chlorinated phenol and a silver compound including, but not limited to, macrolides, aminoglycosides, penicillins, cephalosporins, quinolones, antifungal agents, chlorhexidine or biguanides other than chlorhexidine, chlorinated phenols, sulfonamides, quarternary ammonium compounds, picloxydine, phenolic compounds (e.g., orthophenylphenol), and polymeric quarternary ammonium compounds. Examples of specific agents which can be used include rifampicin, gramicidin, gentamycin, fusidic acid, miconazole, norfloxacin, polymixin, sulfamylon, furazolidine, alexidine, octenidine hydrochloride, cetrimide, polyhexamethylene biguanide, triclocarban, benzalkonium chloride, minocycline, iodinc and iodine complexes such as povidone iodine, pluronic-iodine complex, benzoic acid, sorbic acid, and ethylenediamine tetraacetic acid (EDTA).

These agents used in addition to the triclosan and/or other chlorinated phenol and silver compound combination provide an effective broad spectrum anti-microbial field of activity initially, which inactivates pathogens that otherwise can heavily contaminate the sterile field during implantation. For a non-limiting specific example, see Section 15.

The anti-adherent surface of these devices continues to prevent adherence of microbes that may enter the device tract during and subsequent to implantation. Once these additional agents are diffused out of the devices, the anti-adherent surface continues to prevent adherence of microbes which may contact the device surface through hematogenous seeding or contaminated infusate. Further, without being bound to any particular theory, it is believed that sustained and prolonged release of the anti-microbial agents occurs from the putative triclosan-silver compound complex which provides a longer period of protection.

4.10 MEDICAL ARTICLES COMPRISING A HYDROGEL

According to the present invention, it has been determined that the use of hydrogel polymers increases the antimicrobial efficacy of hydrophilic or hydrophobic matrix systems. In a particular embodiment, the present invention provides for a hydrophilic or hydrophobic medical article which has been impregnated, coated or impregnated and coated with a treatment solution comprising (i) a hydrophilic or hydrophobic polymer, (ii) one or more metal compounds comprising metal atoms or ions or complexes comprising a metal atom or ion selected from the group consisting of silver, copper, zinc, calcium, aluminum and magnesium, (iii) triclosan or other chlorinated phenol, and (iv) a hydrogel. Such medical articles may further comprise, or the treatment solution may comprise, a biguanide such as chlorhexidine or a chlorhexidine salt. In other embodiments, the present invention provides for a metallic or ceramic medical article coated with a treatment solution of (i) to (iv) as set out above. In a preferred embodiment, the hydrogel comprises polyvinyl pyrrolidone ("PVP"). In another preferred embodiment, the hydrophobic polymer polyvinyl chloride ("PVC") may be used to create a hydrophobic matrix into which PVP and antimicrobial agents may be impregnated. Other useful hydrogels that may be used to promote enhanced antimicrobial efficacy include polyethylene oxide, pluronics, ethyl and methyl cellulose, hydroxy ethyl and hydroxy methyl cellulose, incroquats, and polyhydroxyethyl methacrylate.

For a specific, non-limiting example, see Section 19, below.

The following working examples are intended to illustrate but not to limit the scope of the present invention.

5.0 EXAMPLE: TRICLOSAN IMPROVES THE SOLUBILITY OF SILVER COMPOUNDS

Table 1 illustrates the solubility of the silver salt, silver carbonate, mixed at various molar ratios with ammonia, which is used in a treatment solution, in the absence and the presence of triclosan at various molar ratios. Table 2 illustrates the solubility of the silver salt, silver oxide, mixed at various molar ratios with ammonia in the absence and presence of triclosan at various molar ratios. The solubility results demonstrated in Tables 1 and 2 indicate that silver salts are much more soluble in the presence of triclosan, which suggests that the silver compound and triclosan may form a complex.

When ammonia and silver carbonate were mixed at a high molar ratio of 400 to 10, the silver salt remained insoluble in the solvent system. In contrast, in the presence of 30 $\mu$mole of triclosan, the molar ratio of ammonia to silver carbonate needed to solubilize was 50 to 10. Achieving a low molar ratio of ammonia to silver salt is preferred because the surface of devices impregnated with a solvent system containing higher amounts of ammonia can be damaged, thereby enhancing the likelihood of microbial adherence to the surface. In the case of silver oxide, only 10 $\mu$mole of ammonia was needed to solubilize more than 90% of 10 $\mu$mole of silver oxide in the presence of 10 $\mu$mole of triclosan. Further, only 20 $\mu$mole of triclosan was needed to completely solubilize 10 $\mu$mole of silver oxide in the presence of only 10 $\mu$mole of ammonia.

TABLE 1

| Silver Carbonate ($\mu$mole) | Ammonia ($\mu$mole) | Triclosan ($\mu$mole) | Solubility |
|---|---|---|---|
| 10 | 100 | 0 | Not Soluble |
| 10 | 200 | 0 | Not Soluble |
| 10 | 300 | 0 | Not Soluble |
| 10 | 400 | 0 | Not Soluble |
| 10 | 0 | 30 | Not Soluble |
| 10 | 50 | 10 | Partially Soluble |
| 10 | 100 | 10 | Partially Soluble |
| 10 | 150 | 10 | Soluble |
| 10 | 75 | 20 | Partially Soluble |
| 10 | 50 | 30 | Soluble |

TABLE 2

| Silver oxide ($\mu$mole) | Ammonia ($\mu$mole) | TC ($\mu$mole) | Solubility ($\mu$mole) |
|---|---|---|---|
| 10 | 10 | 0 | Not soluble |
| 10 | 100 | 0 | Soluble |
| 10 | 10 | 10 | >90% Soluble |
| 10 | 10 | 20 | Soluble |

6.0 EXAMPLE: EVALUATION OF THE ANTI-MICROBIAL EFFICACY OF TRICLOSAN-SILVER COMPOUND COMBINATIONS IN BROTH CULTURES

The synergistic anti-microbial efficacy of the triclosai/silver compound combination, triclosan/silver sulfadiazine, is illustrated by the results shown in Table 3, and were determined by the following protocol. Drug solutions containing 10% ammonia were prepared in ethanol, and 0.1 ml of each solution was added to 0.9 ml of bacterial culture (50% trypticase soy broth+50% Bovine Calf Serum containing $10^8$ cfu S. aureus/ml). After 10 minutes, a 0.1 ml aliquot was removed and added to 0.9 ml drug inactivating media (LTSB). 0.1 ml from this media was then added to another 0.9 ml of LTSB and 0.2 ml was subcultured on trypticase soy agar plate and incubated at 37° C. for 24 hours. The colony counts were then determined. Control cultures contained similar amounts of ammonia and ethanol as in the test culture.

TABLE 3

| Solution | | Growth in Culture |
|---|---|---|
| Triclosan (%) | Silver Sulfadiazine (%) | (cfu/ml) |
| 0 | 0 | $2.1 \times 10^7$ |
| 0.25 | 0 | $1.2 \times 10^7$ |
| 0.5 | 0 | $1 \times 10^7$ |
| 0 | 0.5 | $5 \times 10^6$ |
| 0 | 1.0 | $1.5 \times 10^6$ |

TABLE 3-continued

| Solution | | Growth in Culture |
|---|---|---|
| Triclosan (%) | Silver Sulfadiazine (%) | (cfu/ml) |
| 0.5 | 0.5 | $8.3 \times 10^5$ |
| 0.5 | 1.0 | $1.4 \times 10^4$ |

These results show the synergistic activity of triclosan and silver sulfadiazine. In the control, in the absence of either triclosan or silver sulfadiazine, there was growth in culture of the magnitude of $2.1 \times 10^7$ cfu/ml. Comparing the relative reduction of growth in culture by the introduction of triclosan and silver sulfadiazine, the addition of triclosan alone at 0.25 and 0.5 percent each resulted in a reduction in growth in culture of less than a power of 10 compared to the control. The addition of silver sulfadiazine alone at 0.5 and 1.0 percent each resulted in a 1 log reduction of growth in culture compared to the control.

Comparing the relative reduction of growth in culture by the introduction of triclosan and silver sulfadiazine in combination, the combination of 0.5 percent triclosan and 0.5 percent silver sulfadiazine resulted in a 2 log reduction in growth in culture compared with the control. The combination of 0.5 percent triclosan and 1.0 percent silver sulfadiazine resulted in a 3 log reduction in cell growth in culture compared with the control. Moreover, the addition of 0.5 percent of silver sulfadiazine from 0.5 to 1.0 in the presence of 0.5 triclosan resulted in a 1 log reduction in growth in culture, whereas the increase of 0.5 to 1.0 percent silver sulfadiazine in the absence of triclosan did not result in a significant decrease. The cell growth in culture in the presence of 0.5 percent triclosan alone added to the cell growth in culture in the presence of 0.5 percent of silver sulfadiazine, the combined presence of 0.5 triclosan and 1.0 silver sulfadiazine resulted in a 3 log reduction in growth in culture, and the increase of 0.5 to 1.0 percent silver sulfadiazine compared to the growth in culture at 0.5 percent triclosan results in a 1 log decrease.

The effects of triclosan and silver carbonate combinations on *S. aureus* growth in culture were also determined using the same protocol. The results are presented in Table 4.

TABLE 4

| Solution | | Growth in Culture |
|---|---|---|
| Triclosan (%) | Silver Carbonate (%) | (cfu/ml) |
| 0 | 0 | $5 \times 10^7$ |
| .25 | 0 | $2 \times 10^7$ |
| .5 | 0 | $1.2 \times 10^7$ |
| 0 | .06 | $1 \times 10^5$ |
| 0 | .125 | $2 \times 10^3$ |
| 0 | .25 | $5 \times 10^2$ |
| .5 | .06 | $3.2 \times 10^4$ |
| .5 | .125 | 0 |
| .5 | .25 | 0 |

The results shown in Table 4 illustrate the synergistic activity of triclosan and silver carbonate. In the control, in the absence of both triclosan and silver carbonate the growth in cell culture was of the magnitude of $5 \times 10^7$ cfu/ml. Combining 0.5 percent triclosan and 0.25 percent silver carbonate resulted in a 7 log reduction in growth in culture. The addition of 0.5 percent triclosan alone resulted in a 0 log reduction, and the addition of 0.25 silver carbonate alone resulted in a 5 log reduction. Therefore one would expect a 5 log reduction of growth in cell culture upon combining the two compositions. However, due to a synergistic activity present when triclosan is combined with silver carbonate an additional 2 log reduction was observed.

Alone, 0.06 percent and 0.125 percent silver carbonate caused a 2 log and a 4 log reduction in growth in culture, respectively, and 0.5 percent triclosan alone caused a 0 log reduction. However, 0.06 percent and 0.125 percent silver carbonate each combined with 0.5 percent triclosan resulted in, respectively, a 3 log reduction and a 7 log reduction of growth in culture.

7.0 EXAMPLE: ANTIMICROBIAL EFFICACY OF CATHETERS IMPREGNATED WITH (1) TRICLOSAN, SILVER SALTS AND VARIOUS ORGANIC ACIDS AND (2) TRICLOSAN, SILVER SALTS AND CHLORHEXIDINE

Catheters impregnated with triclosan, silver compounds and various organic acids, with and without chlorhexidine, were evaluated for effectiveness and duration of antimicrobial efficacy. Treatment solutions comprising triclosan, a silver compound, and an organic acid or chlorhexidine as well as polyurethane polymers were prepared by first dissolving the triclosan, silver compound, and acid or chlorhexidine in methanol, dissolving the polymers in THF, and then mixing the methanol solution with the THF solution in a 30% v/v methanol solution/70% v/v THF solution solvent system. Polyurethane central venous catheter segments were then dipped for one minute in the treatment solution, then allowed to dry. The final concentrations (percentages based on w/v) of active agents and polymers in the treated catheters are set forth in Table 5.

In related experiments, polyurethane catheter segments were treated by a two-step process. In the first step, catheters were dipped in a 70% v/v THF+30% v/v reagent alcohol treatment solution having final concentrations of 3% w/v 93A polyurethane and 1% 60D polyurethane, either with or without silver carbonate at a final concentration of 0.6% (the various components were dissolved in either THF or reagent alcohol before mixing the two to produce the treatment solution, as set forth above). The catheters were allowed to dry. Then, in the second step, the catheters were soaked for one minute in a 20% v/v THF+80% v/v methanol solvent mixture containing either triclosan alone, triclosan and citric acid, or triclosan and chlorhexidine at concentrations set forth in Table 6.

The zones of inhibition were studied against *S. epidermidis* and *P. aeruginosa* over a two day period. The results, shown in Tables 5 and 6, indicate that the combination of citric acid, triclosan and silver compound (silver carbonate) resulted in superior antimicrobial activity against *Pseudomonas aeruginosa*, compared to other organic acids tested.

TABLE 5

| | Zones of Inhibition (mm) | | | |
|---|---|---|---|---|
| | *S. epidermidis* | | *P. aeruginosa* | |
| Treatment Solution | Day 1 | Day 2 | Day 1 | Day 2 |
| 6% TC + 0.6% $Ag_2CO_3$ + 3% 93A PU + 1% 60D PU | 20 | 18 | 9 | 0 |
| 6% TC + 0.6% $Ag_2CO_3$ + 2% salicylic acid + 3% 93A PU + 1% 60D PU | 20 | 18 | 11 | 0 |

TABLE 5-continued

| | Zones of Inhibition (mm) | | | |
| --- | --- | --- | --- | --- |
| | S. epidermidis | | P. aeruginosa | |
| Treatment Solution | Day 1 | Day 2 | Day 1 | Day 2 |
| 6% TC + 0.6% Ag$_2$CO$_3$ + 2% mandelic acid + 3% 93A PU + 1% 60D PU | 20 | 18 | 8 | 0 |
| 6% TC + 0.6% Ag$_2$CO$_3$ + 2% deoxycholic acid + 3% 93A PU + 1% 60D PU | 20 | 18 | 8 | 0 |
| 6% TC + 0.6% Ag$_2$CO$_3$ + 2% citric acid + 3% 93A PU + 1% 60D PU | 20 | 19 | 11 | 8 |
| 6% TC + 0.3% Ag$_2$CO$_3$ + 2% CHX + 3% 93A PU + 1% 60D PU | 21 | 20 | 13 | 12 |

TABLE 6

| | | Zones of Inhibition (mm) | | | |
| --- | --- | --- | --- | --- | --- |
| First Step | Second Step | S. epidermidis | | P. aeruginosa | |
| Treatment Solution | Treatment Solution | Day 1 | Day 2 | Day 1 | Day 2 |
| 3% 93A PU + 1% 60D PU | 6% TC + 4% Citric acid | 20 | 18 | 0 | 0 |
| 3% 93A PU + 1% 60D PU + 0.6% Ag$_2$CO$_3$ | 6% TC | 20 | 18 | 9 | 0 |
| 3% 93A PU + 1% 60D PU + 0.6% Ag$_2$CO$_3$ | 6% TC + 4% Citric acid | 20 | 18 | 10 | 7 |
| 3% 93A PU + 1% 60D PU | 6% TC + 2% CHX | 21 | 17 | 12 | 11 |

8.0 EXAMPLE: METHODS OF PREVENTING ADHERENCE ON MEDICAL ARTICLES

The following techniques were used to impregnate 93A polyurethane catheter segments with triclosan and various silver compounds. The resulting surface characteristics, scored on a scale of 1 to 4, with 4 being the most lubricious surface, are shown in Tables 7 and 8. Soaking time varied from 15 seconds to 1 hour.

Method A: The outer surfaces of catheter segments were impregnated by dipping the segments in a treatment solution of 70% v/v THF (containing 93A polyurethane and 60D polyurethane)+30% v/v (2:1 reagent alcohol:ammonia containing triclosan and silver compound), having final concentrations of 3% w/v 93A polyurethane, 1% w/v 60D polyurethane, 0.3% w/v silver atom or ion, and 6% w/v triclosan.

Method B: Catheter segments had their ends sealed and were soaked for 5 minutes in a treatment solution of 90% v/v (8:1 reagent alcohol/ammonia containing triclosan and silver compound)+10% THF, having final concentrations of 6% w/v triclosan and 0.3% silver (atom or ion).

Method C: The ends of the catheter segments were sealed and the segments were dipped in a treatment solution of 70% v/v THF (containing 60D polyurethane)+30% v/v reagent alcohol having a final concentration of 2% w/v 60D polyurethane. The catheter segments were then dried for one hour, and then were soaked for 5 minutes in a treatment solution of 90% v/v (8:1 ethanol/ammonia containing triclosan and silver compound)+10% THF, having final concentrations of 6% w/v triclosan and 0.3% silver (the treatment solution used in Method B).

Method D: Catheter segments were dipped in a treatment solution of 70% v/v THF (containing 93A polyurethane and 60D polyurethane)+30% v/v (2:1 reagent alcohol:ammonia containing a silver compound), having final concentrations of 3% w/v 93A polyurethane, 1% w/v 60D polyurethane, and 0.3% w/v silver (atom or ion) (the treatment solution used in Method A, but without the triclosan).

The surface characteristics of catheter segments treated according to Methods A–D are shown in Table 7.

TABLE 7

| | Surface Characteristics | | | |
| --- | --- | --- | --- | --- |
| Silver Salt | A | B | C | D |
| 0 (only triclosan) | 3 | 3 | 4 | — |
| Silver carbonate | 4 | 4 | 4 | 3 |
| Silver deoxycholate | 4 | 4 | 4 | Rough |
| Silver oxide | 4 | 4 | 4 | 3 |
| Silver salicylate | 4 | 4 | 4 | 2 |
| Silver iodide | 3 | 3 | 3 | 2 |
| Silver sulfadiazine | 3 | 2 | 2 | 2 |
| Silver nitrate | 4 | 4 | 4 | 4 |

Table 8 shows the results when the outer surfaces of catheter segments were impregnated by dipping the catheters in a treatment solution of 70% v/v THF (containing 93A and 60D polyurethanes) and 30% v/v reagent alcohol (containing triclosan, an organic acid, and a silver compound), having final concentrations of 3% w/v 93A polyurethane, 1% w/v 60D polyurethane, 0.3% w/v silver (atom or ion), 6% w/v triclosan, and 1% w/v organic acid.

TABLE 8

| Metal Salts and Acid in TC Complex | Surface Characteristics |
| --- | --- |
| Silver carbonate + salicylic acid | 3.5 |
| Silver carbonate + deoxycholic acid | 3.5 |
| Silver sulfadiazine + salicylic acid | 3 |
| Silver sulfadiazine + deoxycholic acid | 3 |
| Silver carbonate + citric acid | 4 |
| Silver sulfadiazine + citric acid | 4 |
| Silver sulfadiazine + palmitic acid | 3.5 |
| Silver sulfadiazine + propionic acid | 3.5 |
| Silver sulfadiazine + aspartic acid | 3.5 |

9.0 EXAMPLE: ANTI-MICROBIAL POLYURETHANE CATHETERS PREPARED BY A SHORTER SOAKING TIME (15 SECONDS) AND HIGHER TRICLOSAN LEVELS (UP TO 15%) IN THE IMPREGNATION SOLUTION

A shorter soaking time is preferred in a drug/solvent system since it is less likely to negatively affect the physical integrity of a polymeric device, particularly a polyurethane catheter. In order to attain sufficient drug uptake using a shorter soaking time, it is preferred to increase the amount of triclosan in solution to a range of 10% to 15%. For example, polyurethane catheters were dipped in a solution containing 2% 60D polyurethane dissolved in 70% THF+30% reagent alcohol and allowed to dry for 1 hour. They wore then soaked for 15 seconds in a solution prepared by dissolving enough triclosan and AgNO$_3$ in an 8:1 reagent alcohol/ammonia solution such that when a treatment solution was prepared containing 10% THF and 90% of the reagent alcohol/ammonia/triclosan/AgNO$_3$, the treatment solution contained 15% triclosan and 0.48% AgNO$_3$. As a comparison, catheters were prepared as above with the following changes: the triclosan concentration was reduced to 6% and the soaking time was increased to 1 minute. The initial drug levels, measured spectrophotometrically, and zones of inhibition against S. epidermidis and P. aeruginosa were determined for catheter samples of both groups and are shown in Table 9.

TABLE 9

| Treatment | μg TC/cm | Zones of Inhibition (mm) vs. S. epidermidis | vs. P. aeruginosa |
|---|---|---|---|
| 15 sec × (15% TC + 0.48% AgNO$_3$) | 436 | 11 | 4 |
| 1 min × (6% TC + 0.48% AgNO$_3$) | 410 | 13 | 4 |

As illustrated in Table 9, both initial drug uptake and zone of inhibition data indicate that a similar efficacy is obtainable using a higher concentration of drug and a shorter soaking time. In addition, a shorter soaking time in a drug/solvent system is less likely to negatively affect the physical integrity of the device.

10.0 EXAMPLE: IMPREGNATION OF TRICLOSAN-SILVER COMBINATION IN LATEX URINARY CATHETER AND PTFE SOFT TISSUE PATCHES (STP)

Segments of latex urinary catheters and PTFE soft tissue patches (STP) were impregnated by soaking these materials (or suctioning under vacuum in the case of PTFE STP) for 1 hour in a treatment solution prepared by mixing 80% v/v THF and 10% v/v reagent alcohol/10% v/v ammonia (containing triclosan and silver carbonate), having final concentrations of 1% w/v triclosan and 0.2% w/v silver carbonate. The impregnated materials were dried and then rinsed in water and dried again. The antimicrobial properties of the material were then tested by measuring the zones of inhibition produced against S. aureus, P. aeruginosa, F. aerogenes and C. albicans after placing the treated material on a trypticase soy agar plate seeded with 0.3 ml of $10^8$ cfu/ml bacterial or yeast culture and incubating at 37° C. for 24 hours. The results are shown in Table 10.

TABLE 10

| | Zones of inhibition (mm) | |
|---|---|---|
| | Urinary Catheter | STP |
| S. aureus | 21 | >30 |
| P. aeruginosa | 6 | 7 |
| E. aerogenes | 10 | 25 |
| C. albicans | 7 | 12 |

11.0 EXAMPLE: ANTIMICROBIAL EFFICACY OF SUBCUTANEOUS CUFFS CONTAINING FABRICS CONSISTING OF DACRON, ACRYLIC AND PTFE

The antimicrobial efficacy of subcutaneous cuff material containing fabrics made of Dacron, Acrylic and PTFE were impregnated with a treatment solution prepared by mixing 10% v/v ammonia/10% v/v reagent alcohol (containing silver carbonate, triclosan and chlorhexidine) and 80% v/v THF (containing 93A and 60D polyurethanes), having final concentrations of 4% w/v 93A polyurethane, 1% w/v 60D polyurethane, 0.2% w/v silver carbonate, 0.1% w/v triclosan and 0.5% w/v chlorhexidine, The resulting material was then dried for 24 hours and the zones of inhibition against S. aureus and P. aeruginosa were determined. The zones of inhibition are shown in Table 11.

TABLE 11

| | Zone of Inhibition (mm) | |
|---|---|---|
| Cuff Material | S. aureus | P. aeruginosa |
| Dacron | 20 | 12 |
| Acrylic | 19 | 12 |
| PTFE | 18 | 10 |

12.0 EXAMPLE: METHOD OF IMPREGNATION OF LEFT VENTRICULAR ASSIST DEVICE (LVAD) DRIVE LINES

Left ventricular assist device (LVAD) drive lines, which are made of Dacron material and are attached to silicone tubing, were impregnated with a polymeric matrix containing triclosan and silver salts.

Dacron material was treated with one of two different treatment solutions as follows.

In a first case, Dacron material was uniformly spread with a treatment solution which was 10% v/v ammonia, 10% v/v reagent alcohol (containing silver carbonate and triclosan)+ 80% THF (containing 93A and 60D polyurethanes), having final concentrations of 0.2% w/v silver carbonate, 0.1% w/v triclosan, 4% w/v 93A polyurethane, and 1% w/v 60D polyurethane. As in previous examples, the silver carbonate and triclosan were first dissolved in 1:1 ammonia/reagent alcohol, and the polyurethanes were first dissolved in THF, and then the ammonia/reagent alcohol and THF were mixed to achieve the proper final ratios.

In a second case, Dacron material was uniformly spread with a treatment solution which was 10% v/v ammonia, 10% v/v reagent alcohol (containing silver carbonate, triclosan and chlorhexidine)+80% THF (containing 93A and 60D polyurethanes), having final concentrations of 0.2% w/v silver carbonate, 0.5% w/v chlorhexidine, 0.1% w/v triclosan, 4% w/v 93A polyurethane, and 1% w/v 60D polyurethane.

Dacron material having a polymer-drug film prepared as above was then attached to silicone tubing, thereby creating a drive line, and dried. This method is particularly important for devices in which tissue ingrowth is intended to occur after implantation (e.g., cuffs). Antimicrobial activity was evaluated after 24 hours by measuring the zones of inhibition produced by placing 0.25 cm length of drive line on trypticase soy agar seeded with 0.3 ml of $10^8$ cfu/ml bacteria and incubated at 37° C. for 24 hours. The zones of inhibition were measured after 24 hours, and the results are shown in Table 12.

TABLE 12

| | Zones of Inhibition (mm) | |
|---|---|---|
| Drugs in Catheter | S. aureus | P. aeruginosa |
| 0.2% Ag$_2$CO$_3$, 0.1% TC | 16 | 6 |
| 0.2% Ag$_2$CO$_3$, 0.1% TC, 0.5% CHX | 20 | 12 |

As shown in Table 12, drive line treated with polymer, silver carbonate, and low levels of triclosan had antimicrobial activity against both S. aureus and P. aeruginosa. The antimicrobial effect was improved by the addition of chlorhexidine.

In related experiments, subcutaneous cuffs containing fragments consisting of Dacron, acrylic or PTFE were impregnated by dipping in a treatment solution which is 10% v/v ammonia, 10% v/v reagent alcohol (containing silver carbonate, triclosan and chlorhexidine)+80% THF (containing 93A and 60D polyurethanes), having final concentrations of 0.2% w/v silver carbonate, 0.5% w/v chlorhexidine, 0.1% w/v triclosan, 4% w/v 93A polyurethane, and 1% w/v 60D polyurethane. The treated material was allowed to dry, and then tested for antimicrobial activity as set forth above. The results are shown in Table 13.

TABLE 13

| Cuff Material | Zone of Inhibition (mm) | |
|---|---|---|
| | S. aureus | P. aeruginosa |
| Dacron | 20 | 12 |
| Acrylic | 19 | 12 |
| PTFE | 18 | 10 |

13.0 EXAMPLE: BACTERIAL ADHERENCE ON TRICLOSAN-SILVER COMPOUND IMPREGNATED CATHETERS POST IMPLANTATION IN RATS

The ability of catheters impregnated with triclosan and a silver compound to resist bacterial adherence was tested by introducing and maintaining treated catheters in vivo in rats, removing the catheters, exposing the catheters to bacterial cultures, and then measuring the amount of bacteria adhered to the extracted catheter segments.

The catheter segments were impregnated with triclosan and various silver compounds and/or chlorhexidine diacetate (CHA), using treatment solutions having the final concentrations of agents set forth in Table 14, below. In each case, the amount of silver compound in the treatment solution contributed silver atom/ion at a concentration of 0.3% w/v. The treatment solutions comprised THF and reagent alcohol mixed solutions, where polyurethane components were dissolved in the THF and triclosan and silver compounds were dissolved in the reagent alcohol prior to mixing. The amount of THF/polyurethane was generally 70% (v/v). The amount of reagent alcohol was 30% (v/v). Where indicated by an asterisk in Table 16, the solvent was simply reagent alcohol; otherwise, the solvent system was reagent alcohol/ammonia in a 2:1 ratio (accounting for 20% and 10%, respectively, on a volume to volume basis). Polymers in the treatment solutions were initially dissolved in the THF component and had final concentrations of 3% w/v 93A polyurethane and 1% w/v 60D polyurethane. Catheter segments were dipped in the treatment solution, and then dried for three days prior to use. Unimpregnated catheter segments were used as controls.

Six 3 cm segments of catheters from each catheter group were implanted in a subcutaneous pocket on the dorsal side of laboratory rats. After seven days the catheters were removed and rinsed twice in saline and processed as follows: Each group of catheter segments (6×3 cm) were transferred to 18 ml of 10% BCS+90% TSB containing 3.0 ml of $10^7$ cfu S. epidermidis/ml at 37° C. in a rotary shaker for 4 hours. Then the catheters were removed, blotted, rinsed twice in saline, blotted and rolled over the surface of drug neutralizing agar plates (D/E plates) and incubated for 24 hrs at 37° C. The colony counts observed in Table 14 were then determined for each catheter group.

TABLE 14

| Agents In Treatment Solution | No. of Catheter Segments Not Colonized | Catheter Segments Colonized ($10^2$–$10^4$ cfu/cm) |
|---|---|---|
| 6% TC + 0.75% AgSD | 0 | 6 |
| 6% TC + 0.79% Ag paraamino salicylic acid | 0 | 6 |
| 6% TC + 0.8% Ag acetylsalicylic acid | 0 | 6 |
| 0.75% AgSD + 4% CHA* | 0 | 5 |
| 6% TC + 0.6% Ag salicylate | 1 | 5 |
| 6% TC + 0.8% Ag laurate | 1 | 5 |
| 6% TC + 1.5% Ag deoxycholate | 1 | 5 |
| 6% TC | 1 | 4 |
| 6% TC + 0.32% Ag oxide | 2 | 4 |
| 6% TC + 1% Ag Paraamino benzoic acid | 3 | 3 |
| 6% TC + 0.4% Ag Carbonate | 4 | 2 |
| 6% TC + 0.48% Ag Nitrate | 5 | 1 |
| 6% TC + 0.4% Ag Carbonate* | 5 | 1 |
| control 1 | 0 | 4 |
| control 2 | 1 | 5 |

*solution does not contain ammonia

As evidenced from the results of Table 14, the catheter groups containing triclosan-silver salt combinations were effective in preventing bacterial adherence on catheters after being implanted for seven days in rats.

A further two sets of experiments were carried out to determine the antimicrobial efficacy of catheters treated according to the invention. In particular, one set of experiments involved an "initial infection model" where the initial catheter wound site was inoculated with bacteria, and another set of experiments involved a "delayed infection model" in which catheters implanted in rats for ten days were removed and exposed to bacterial cultures in vitro. In these two sets of experiments, the results of which are shown in Table 15, long term and short term efficacy of treated catheters was evaluated and compared.

In experiments involving the "initial infection model", the dorsal side of a rat was shaved and a 7 cm segment of catheter treated with the agents set forth in Table 15 (with both ends sealed with silicone plugs) was implanted subcutaneously through a 0.5 cm incision just above the shoulder area. The catheter was kept in place, and the tract and insertion site were inoculated with 20 µl of bacterial culture having $10^8$ cfu of S. aureus per milliliter. The wound was then closed with surgical clips. After ten days, the catheters were removed and swab cultures of the insertion site and tract were taken. Only the control group had a positive swab culture. Bacterial adherence on the outer surface of the catheters was determined by sonicating the catheters in drug neutralizing media and then subculturing on a trypticase soy agar plate.

In experiments involving the "delayed infection model", catheter segments (3 cm each, with sealed ends, treated with the agents set forth in Table 15, in solvent systems that were 70% v/v THF and 30% v/v reagent alcohol and contained 3% w/v 93A and 1% w/v 60D polytirethanes) were implanted subcutaneously in rats (6 segments of catheters treated with the same agents per rat). After ten days in vivo, the catheters were excised and rinsed twice with saline. Then each group of six segments was incubated in 18 ml of a log-phase culture of *S. epidermidis* ($10^7$ cfu/ml of 10% bovine adult serum+90% TSB) in a rotary shaker for four hours. The bacterial adherence was determined by sonicating the catheters in drug neutralizing media and then subculturing on a trypticase soy agar plate.

Untreated catheters were implanted in rats of both models to serve as controls.

TABLE 15

| Catheter Group | Initial Contamination* | 10 Days Post Contamination* |
|---|---|---|
| Control | $1 \times 10^3$ | $>10^5$ |
| 1.5% CHA + 0.75% AgSD | 10 | $5 \times 10^5$ |
| 2% CHA + 2% TC + 0.75% AgSD | 0 | $1 \times 10^4$ |
| 6% TC + 0.36% AgNO$_3$ | 33 | 26 |
| 6% TC + 0.4% Ag$_2$CO$_3$ | 90 | $1 \times 10^2$ |
| 6% TC + 0.75% AgSD | Not Done | $1 \times 10^4$ |

*colony forming units (cfu) per 1 cm catheter.

As shown in Table 15, triclosan/silver nitrate and triclosan/silver carbonate treated catheter surfaces were found to be more lubricious (as indicated by lower cfu associated with catheters 10 days post-implantation), even though their antimicrobial activity appeared to be lower than that of chlorhexidine/silver sulfadiazine or chlorhexidine/triclosan/silver sulfadiazine treated catheters (as reflected by lower cfu in the initial contamination models). It appears from these results that surface characteristics play an important role in the prevention of delayed infection. Chlorhexidine containing catheters were more effective in preventing initial infections while triclosan/silver compound catheters were more effective in preventing later infections. The latter catheters showed significantly lower bacterial adherence compared to control catheters when infected initially.

14.0 EXAMPLE: ABILITY OF TREATED PTFE PATCHES TO RESIST INFECTION IN AN ANIMAL MODE

The ability of PTFE soft tissue patches, treated with combinations of triclosan and/or chlorhexidine and the silver salt, silver carbonate, to resist infection was tested as follows. Disks of PTFE patches were impregnated with treatment solutions prepared by dissolving triclosan and/or chlorhexidine and silver carbonate in 1:1 reagent alcohol/ammonium hydroxide, and then mixing with THF to produce a 80% v/v THF, 10% reagent alcohol, 10% v/v ammonium hydroxide solution having triclosan, chlorhexidine, and silver carbonate final concentrations as specified in Table 16 below. The patch material was soaked in treatment solution for 1 hour under a vacuum. The patches were implanted subcutaneously in a pocket in the abdominal area of rats and infected with 10 μl of $10^8$ CFU *S. aureus*. After 7 days, they were removed and bacterial adherence was determined by sonicating the catheters in drug neutralizing media and then subculturing on a trypticase soy agar plate. The efficacy of patches in resisting infection due to contamination at the time of implantation is illustrated by the bacterial adherence data provided in Table 16.

TABLE 16

| Impregnation Solution | Bacterial Adherence CFU/DISK |
|---|---|
| 0.25% TC + 0.2% Ag$_2$CO$_3$ + 0.5 CHX | 4 |
| 1.0% TC + 0.2% Ag$_2$CO$_3$ | 1 |
| 0.5% CHX + 0.2% Ag$_2$CO$_3$ | 15 |
| 0.5% TC + 0.25% CHA + 0.25% CHX | 15 |
| Unimpregnated | $7.6 \times 10^3$ |

As shown in Table 16, all of the above groups with and without chlorhexidine were observed to be similarly efficacious relative to the control, unimpregnated group.

15.0 EXAMPLE: ENHANCEMENT OF THE ANTI-MICROBIAL ACTIVITY OF DEVICES CONTAINING SILVER AND TRICLOSAN USING OTHER SOLUBLE ANTI-INFECTIVE AGENTS

Polyurethane catheter segments were impregnated by dipping in a treatment solution prepared by mixing 10% v/v ammonia/20% v/v reagent alcohol (containing triclosan, silver carbonate, and, except for the control, an additional antibiotic) with 70% v/v THF (containing 93A and 60D polyurethanes), having final concentrations of 3% w/v 93A polyurethane, 1% w/v 60D polyurethane, 6% w/v triclosan, 0.4% w/v Ag$_2$CO$_3$ and 0.5% of the antibiotics set forth in Table 17, below. The treated catheter segments were then dried for 24 hours and evaluated for antimicrobial activity by determining the zones of inhibition created in cultures of various microbes. The antimicrobial properties of the material were then tested by measuring the zones of inhibition produced against *S. aureus, P. aeruginosa, E. aerogenes* and *C. albicans* after placing the treated material on a trypticase soy agar plate seeded with 0.3 ml of $10^8$ cfu/ml bacterial/yeast culture and incubating at 37° C. for 24 hours.

Table 17 shows the enhanced effective broad spectrum anti-microbial field around a catheter produced by the addition of soluble anti-infective agents. Using antibiotics along with the triclosan-silver salt combination may reduce the risk of development of antibiotic resistant microbes.

TABLE 17

| Agents in Treatment Solution | Zones of Inhibition (mm) | | | |
|---|---|---|---|---|
| | *S. aureus* | *P. aeruginosa* | *E. aerogens* | *C. albicans* |
| 6% TC + 0.4% Ag$_2$CO$_3$ + 0.5% Gramicidin | 14 | 6 | 7 | 7 |
| 6% TC + 0.4% Ag$_2$CO$_3$ + 0.5% Polymixin | 17 | 16 | 15 | 7 |
| 6% TC + 0.4% Ag$_2$CO$_3$ + 0.5% Norfloxacin | 19 | 18 | 18 | 10 |
| 6% TC+ 0.4% Ag$_2$CO$_3$ + 0.5% Sulfamylon | 12 | 12 | 13 | 9 |
| 6% TC + 0.4% Ag$_2$CO$_3$ + 0.5% Rifampicin | 21 | 5 | 5 | 0 |
| 6% TC + 0.4% Ag$_2$CO$_3$ + NO ANTIBIOTIC (CONTROL) | 13 | 6 | 6 | 5 |

16.0 EXAMPLE: ANTIMICROBIAL ACTIVITY OF VARIOUS TRICLOSAN-SILVER COMPOUND COMBINATIONS

Polyurethane catheter segments were treated by dipping in a treatment solution having final concentrations of triclosan and/or silver compound as set forth in Table 18, below, where the solvent system was 70% v/v THF and 30% v/v reagent alcohol and contained 3% w/v 93A and 1% w/v 60D polyurethanes. Six catheter segments from each group were placed vertically on a trypticase soy agar plate seeded with 0.3 ml of $10^8$ cfu/ml bacterial/yeast culture and incubated at 37° C. for 24 hours. The results are shown in Table 18.

TABLE 18

| Drug in Impregnation Solution | Zones of Inhibition (mm) | | | |
|---|---|---|---|---|
| | S. aureus | P. aeruginosa | Enterobacter aerogenes | Candida albicans |
| 6% TC | 15 | 0 | 6 | 0 |
| 1% AgSD | 8 | 5 | 0 | 0 |
| 0.5% Ag$_2$CO$_3$ | 8 | 7 | 0 | 6 |
| 0.6% AgSalicylate | 9 | 6.5 | 0 | 7.3 |
| 0.32% Ag Oxide | 9 | 7 | 0 | 11 |
| 1.5% Ag Deoxycholate | 1 | 4 | 0 | 5 |
| 6% TC + 1% AgSD | 17 | 6 | 5 | 5 |
| 6% TC + 0.5% Ag$_2$CO$_3$ | 22 | 9 | 6 | 7 |
| 6% TC + 0.6% Ag Salicylate | 20 | 10 | 7 | 11 |
| 6% TC + 0.32% Ag Oxide | 22 | 10 | 6 | 15 |
| 6% TC + 1.5% Ag Deoxycholate | 17 | 7 | 5 | 10 |
| 2% TC + 1% AgSD + 2% CHX | 17 | 11 | 12 | 13 |
| 6% TC + 0.7% Ag ParaaminoBenzoate acid | 17 | 7 | 6 | 5 |
| 6% TC + 0.79% Ag Paraamino Salicylate | 19 | 7 | 6 | 4 |
| 6% TC + 0.8% Ag AcetylSalicylate | 19 | 8 | 7 | 9 |
| 0.7% Ag Paraamino Benzoate | 3.5 | 4.0 | 0 | 0 |
| 0.79% Ag ParaaminoSalicylate | 5.5 | 7.5 | 3.3 | 0 |
| 0.8% Ag Acetyl Salicylate | 7.0 | 8.0 | 4.7 | 0 |

It is noted that the combination of triclosan with either silver paraaminobenzoate, silver paraaminosalicylate, or silver acetylsalicylate resulted in unexpected efficacy against *C. albicans* as compared with each of the agents tested alone. Also illustrated by Table 18 is the synergistic effect achieved by the presence of triclosan in combination with silver salts.

17.0 EXAMPLE: IMPREGNATION OF ANTI-INFLAMMATORY AGENTS ALONG WITH TRICLOSAN AND SILVER SALTS

The following experiments demonstrated that the addition of the anti-inflammatory agent salicylic acid and its derivatives to combinations of triclosan and silver compounds improved antimicrobial activity.

LVAD drive lines made of Dacron were impregnated with triclosan, silver sulfadiazine and chlorhexidine, with or without salicylic acid, as follows. One set of pieces of Dacron were uniformly spread with a treatment solution prepared by mixing 30% v/v reagent alcohol (containing triclosan (TC), silver sulfadiazine (AgSD), and chlorhexidine (CHX)) and 70% v/v THF (containing 93A and 60D polyurethanes), having final concentrations of 0.1% w/v triclosan, 0.2% w/v silver sulfadiazine, 0.5% w/v chlorhexidine, 4% w/v 93A polyurethane, and 1% w/v 60D polyurethane. Another set of Dacron pieces were uniformly spread with a second treatment solution having the same components, but also having a final concentration of 0.5% w/v salicylic acid (the salicylic acid being initially dissolved in the reagent alcohol component). As a control, one set of Dacron pieces was treated with a third treatment solution containing salicylic acid and polymer but lacking triclosan, silver sulfadiazine, and chlorhexidine. The Dacron pieces were dried for 24 hours prior to antimicrobial testing.

In an analogous set of experiments, polyurethane catheters were impregnated with triclosan and silver carbonate, with or without salicylic acid or one of its derivatives. One set of polyurethane catheter segments were therefor dipped in a treatment solution prepared by mixing 20% v/v reagent alcohol/10% v/v ammonia (containing triclosan and silver carbonate ) and 70% v/v THF (containing 93A and 60D polyurethanes), having final concentrations of 6% w/v triclosan, 0.4% w/v silver carbonate, 3% w/v 93A polyurethane and 1% w/v 60D polyurethane. Three other sets of catheter segments were treated with the same solution further having a final concentration of 0.5% w/v salicylic acid, 0.5% w/v acetylsalicylic acid, or 0.5% w/v paraaminosalicylic acid, respectively (the salicylic acid or derivative thereof being first dissolved in the ethanol/ammonia solution). As controls, another three sets of catheters were impregnated using treatment solutions as above, containing either 0.5% w/v salicylic acid, 0.5% w/v acetylsalicylic acid, or 0.5% w/v paraaminosalicylic acid and polymer, but lacking triclosan or silver carbonate. The treated catheters were dried for 24 hours prior to antimicrobial testing.

Antimicrobial testing was performed by placing the Dacron drive line or catheter segment on trypticase soy agar seeded with $5 \times 10^8$ cfu of *Pseudomonas aeruginosa*. The zones of inhibition were measured after inclubation of the plates at 37° C. for 24 hours. The results, presented in Table 19, illustrate that both hydrophilic (polyurethane) and hydrophobic (Dacron) medical devices can be rendered infection resistant and that anti-inflammatory agents such as salicylates enhance antimicrobial activity.

TABLE 19

| | Zones of Inhibition (mm) against P. aeruginosa | |
|---|---|---|
| Agents in Treatment Solution | LVAD DriveLine | Polyurethane Catheters |
| 0.1% TC + 0.2% AgSD + 0.5% CHX | 12 | — |
| 0.1% TC + 0.2% AgSD + 0.5% CHX + 0.5% Salicylic acid | 15 | — |
| 0.5% Salicylic Acid | 0 | — |
| 6% TC + 0.4% Ag$_2$CO$_3$ | — | 7 |
| 6% TC + 0.4% Ag$_2$CO$_3$ + 0.5% Salicylic Acid | — | 11 |
| 6% TC + 0.4% Ag$_2$CO$_3$ + 0.5% Acetylsalicylic Acid | — | 11 |
| 6% TC + 0.4% Ag$_2$CO$_3$ + 0.5% Paraaminosalicylic Acid | — | 11 |
| 0.5% Salicylc Acid | — | 0 |
| 0.5% Acetylsalicylic Acid | — | 0 |
| 0.5% Paraaminosalicylic Acid | — | 0 |

18.0 EXAMPLE: ANTI-MICROBIAL EFFICACY OF COMBINATIONS OF SILVER SALTS AND CHLORINATED PHENOLIC COMPOUNDS

Silver compounds, in particular silver salts and various phenolic compounds were combined to study prolonged anti-microbial efficacy of the various compositions. Catheter segments for study were prepared by treating a polyurethane catheter segment in a treatment solution having 70% v/v THF and 30% v/v reagent alcohol and concentrations of 3% w/v 93A polyurethane and 1% w/v 60D polyurethane, having final concentrations of agents set forth in Table 20. Then segments were placed on petri dishes seeded with *Pseudomonas aeruginosa*. Table 3 illustrates the zones of inhibition of *Pseudomonas aeruginosa* over a three day period of $Ag_2CO_3$ and $Ag_2CO_3$ in combination with three phenolic compositions, (1) parachlorometaxylenol (PCMX), (2) o-phenyl phenol and (3) p-tertiary amyl phenol, and compared their respective efficacy to triclosan and $Ag_2CO_3$. As shown in Table 20 it appears that a synergistic effect occurs when chlorinated phenols are combined with silver salt exhibiting prolonged anti-microbial activity.

TABLE 20

| Drugs in Catheter | Zones of Inhibition (mm) DAY | | |
|---|---|---|---|
| | 1 | 2 | 3 |
| 6% triclosan + 0.6% $Ag_2CO_3$ | 11 | 10 | 6 |
| 6% PCMX + 0.6% $Ag_2CO_3$ | 12 | 10 | 7 |
| 6% O-phenyl phenol + 0.6% $Ag_2CO_3$ | 10 | 0 | 0 |
| 6% p-tertiary amyl phenol + 0.6% $Ag_2CO_3$ | 10 | 0 | 0 |
| 0.6% $Ag_2CO_3$ | 10 | 0 | 0 |

19.0 ANTIMICROBIAL EFFICACY OF HYDROPHILIC OR HYDROPHOBIC MATRIX SYSTEMS BY ADDITION OF HYDROGEL POLYMER

We tested the effect on antimicrobial activity of adding a hydrogel polymer such as polyvinyl pyrrolidone (PVP) to treatment solutions containing triclosan, silver compound, and polyurethanes, and then using such solutions to treat medical devices. Polyurethane catheter segments were dipped in one of the following two treatment solutions:

(i) a treatment solution prepared by mixing 30% v/v reagent alcohol (containing triclosan and silver carbonate) with 70% v/v THF (containing 93A and 60D polyurethanes), having final concentrations of 6% w/v triclosan, 0.4% w/v silver carbonate, 3% w/v 93A polyurethane, and 1% w/v 60D polyurethane; or (ii) a treatment solution prepared by mixing 30% v/v reagent alcohol (containing triclosan and silver carbonate) with 70% v/v THF (containing 60D polyurethane and PVP), having final concentrations of 6% w/v triclosan, 0.4% w/v silver carbonate, 3% w/v 60D polyurethane, and 2% w/v PVP.

The treated catheter segments were then dried for 24 hours and then tested for antimicrobial activity by measuring the zones of inhibition The antimicrobial properties of the material were then tested by measuring the zones of inhibition produced against *S. epidermidis* and *P. aeruginosa* after placing the treated material on a trypticase soy agar plate seeded with 0.3 ml of $10^8$ cfu/ml bacterial culture and incubating at 37° C. for 24 hours. In addition, the amount of triclosan present per centimeter of catheter was determined spectrophotometrically. The results are shown in Table 21.

TABLE 21

| | | Zones of Inhibition (mm) | |
|---|---|---|---|
| Compounds in Treatment Solution | μg TC/cm | vs. *S. epidermidis* | vs. *P. aeruginosa* |
| 6% TC + 0.4% $Ag_2CO_3$ + 3% 93A PU + 1% 60D PU | 425 | 11 | 6.5 |
| 6% TC + 0.4% $Ag_2CO_3$ + 3% 60D PU + 2% PVP | 397 | 18 | 10 |

In other experiments, the effect of PVP incorporated into a hydrophobic article, i.e., Dacron material for LVAD drive lines, was determined. In particular, pieces of Dacron were uniformly spread with one of the two following treatment solutions:

(iii) a treatment solution prepared by mixing 10% v/v reagent alcohol (containing triclosan, chlorhexidine diacetate (CHA), chlorhexidine free base (CHX) and silver sulfadiazine) with 90% v/v THF (containing 93A and 60D polyurethanes), having final concentrations of 0.2% w/v triclosan, 0.3% w/v chlorhexidine diacetate, 0.2% w/v chlorhexidine free base, 0.2% w/v silver sulfadiazine, 4% w/v 93A polyurethane, and 1% w/v 60D polyurethane, or (iv) a treatment solution prepared by mixing 10% v/v reagent alcohol (containing triclosan, chlorhexidine diacetate (CHA), chlorhexidine free base (CHX) and silver sulfadiazine) with 90% v/v THF (containing 93A and 60D polyurethanes and PVP and polyvinylchlioride ("PVC")), having final concentrations of 0.2% w/v triclosan, 0.3% w/v chlorhexidine diacetate, 0.2% w/v chlorhexidine free base, 0.2% w/v silver sulfadiazine, 4% w/v 93A polyurethane, 1% w/v 60D polyurethane, 2% w/v PVP and 4% w/v PVC.

The treated Dacron was allowed to dry for 24 hours and then attached to the outer surface of silicon tubing using a silicon adhesive to produce a drive line. The resulting drive lines were then tested for antimicrobial activity by measuring the zones of inhibition produced against *S. epidermidis, P. aeruginosa*, and *C. albicans* after placing the treated material on a trypticase soy agar plate seeded with 0.3 ml of $10^8$ cfu/ml bacterial or yeast culture and incubating at 37° C. for 24 hours. In addition, the amounts of triclosan and chlorhexidine present per centimeter of Dacron were determined spectrophotometrically. The results are shown in Table 22.

TABLE 22

| | | | Zones of Inhibition (mm) | | |
|---|---|---|---|---|---|
| Group | μg TC/cm | μg CHX/cm | v. *S. epidermidis* | v. *P. aeruginosa* | v. *C. albicans* |
| LXI | 387 | 662 | 17 | 11.5 | 14 |
| LXII | 420 | 480 | 22 | 15 | 16 |

As illustrated in Tables 21 and 22, the use of a hydrogel such as PVP in a hydrophilic (e.g., polyurethane) or hydrophobic (e.g., PVC) matrix allows better drug release as evidence by greater zones of inhibition.

Various publications are cited herein, which are hereby incorporated by reference in their entireties.

We claim:

1. An anti-infective medical article prepared by exposing a polymer-containing medical article, for an effective period of time, to a treatment solution comprising between about 0.3 and 1.5 percent of a silver salt and between about 0.1 and 20 percent triclosan, where the treatment solution and the medical article do not contain chlorhexidinie or a chlorhexidine salt.

2. The anti-infective medical article of claim 1, where the treatment solution further comprises an organic acid at a concentration of between about 0.1 and 5 percent.

3. The anti-infective medical article of claim 2, where the organic acid is citric acid.

4. The anti-infective medical article of claim 1, where the treatment solution further comprises an anti-inflammatory agent, at a concentration of between about 1 and 5 percent.

5. The anti-infective medical article of claim 4, where the anti-inflammatory agent is salicylic acid or a derivative thereof.

6. The anti-infective medical article of claim 1, where the treatment solution further comprises an additional antimicrobial agent.

7. The anti-infective medical article of claim 6, where the additional antimicrobial agent is selected from the group consisting of gramicidin, polymixin, norfloxacin, sulfamylon, polyhexamethylene biguanide, alexidine, minocycline, iodine, benzalkonium chloride and rifampicin.

8. The anti-infective medical article of claim 1, where the treatment solution further comprises between about 1 and 5 percent of one or more hydrophilic or hydrophobic polymer.

9. The anti-infective medical article of claim 1 which is a polytetrafluoroethylene patch.

10. A polymer-containing vascular catheter comprising between about 100 and 600 micrograms of triclosan in releasable form per centimeter and between about 25 and 100 micrograms of silver atom or ion in releasable form per centimeter, where the catheter does not contain chliorhexidine or a chlorhexidine salt.

11. A method of preparing an anti-infective medical article comprising exposing a polymer-containing medical article, for an effective period of time, to a treatment solution comprising between about 0.3 and 1.5 percent of a silver salt and between about 0.1 and 20 percent triclosan, where the treatment solution and the medical article do not contain chlorhexidine or a chlorhexidine salt.

12. The method of claim 11, where the treatment solution further comprises an organic acid at a concentration of between about 0.1 and 5 percent.

13. The method of claim 12, where the organic acid is citric acid.

14. The method of claim 11, where the treatment solution further comprises an anti-inflammatory agent, at a concentration of between about 1 and 5 percent.

15. The method of claim 14, where the anti-inflammatory agent is salicylic acid or a derivative thereof.

16. The method of claim 11, where the treatment solution further comprises an additional antimicrobial agent.

17. The method of claim 14, where the additional antimicrobial agent is selected from the group consisting of gramiciain, polymixin, norfloxacin, sulfamylon, polyhexamethylene biguanide, alexidine, minocycline, iodine, benzalkonium chloride and rifampicin.

18. The method of claim 11, where the treatment solution further comprises between about 1 and 5 percent of one or more hydrophilic or hydrophobic polymer.

19. The method of claim 11, where the polymer-containing medical article is a polytetrafluoroethylene patch.

20. An anti-infective medical article prepared by exposing a polymer-containing medical article, for an effective period of time, to a treatment solution comprising between about 0.3 and 1.5 percent of a silver salt and between about 0.1 and 20 percent triclosan, where the treatment solution and the medical article do not contain chlorhexidine or a chlorhexidine salt, and where the article comprises polytetrafluoroethylene polymer.

\* \* \* \* \*

UNITED STATES PATENT AND TRADEMARK OFFICE
CERTIFICATE OF CORRECTION

PATENT NO.   : 6,224,579 B1
DATED        : May 1, 2001
INVENTOR(S)  : Modak et al.

It is certified that error appears in the above-identified patent and that said Letters Patent is hereby corrected as shown below:

Column 1,
Line 38, "application" should read -- applications --.
Line 39, "chliorhexidine" should read -- chlorhexidine --.

Column 2,
Line 30, "copolymerisable" should read -- copolymerizable --.

Column 5,
Line 14, "gtriclosan" should read -- triclosan --.
Line 17, "tricolsan" should read -- triclosan --.
Line 51, "Successftil" should read -- Successful --.
Line 57, "agent-polymcric" should read -- agent-polymeric --.

Column 6,
Line 16, "HYRDOPHILIC" should read -- HYDROPHILIC --.
Line 42, "*Polyurethianes*" should read -- *Polyurethanes* --.
Line 45, "tirethanes" should read -- urethanes --.

Column 9,
Line 42, "trielosan" should read -- triclosan --.

Column 10,
Line 16, "polyactic" should read -- polylactic --.
Lines 55 and 57, "quarternary" should read -- quaternary --.
Line 63, "iodinc" should read -- iodine --.

Column 12,
Line 42, "triclosai/" should read -- triclosan/ --.

Column 13,
Line 36, "sulfadiazinc" should read -- sulfadiazine --.

Column 16,
Line 62, "wore" should read -- were --.

Column 17,
Line 4, "spectrophotomctrically" should read -- spectrophotometrically --.

UNITED STATES PATENT AND TRADEMARK OFFICE
CERTIFICATE OF CORRECTION

PATENT NO.    : 6,224,579 B1
DATED         : May 1, 2001
INVENTOR(S)   : Modak et al.

It is certified that error appears in the above-identified patent and that said Letters Patent is hereby corrected as shown below:

Column 20,
Table 14, rows 7 and 8, align numbers in column 2 and 3 with heading "6% TC"
"6% TC +1.5%      1          5
 Ag deoxycholate  1          4
 6% TC                       "
should read
-- 6% TC +1.5%    1          5
   Ag deoxycholate
   6% TC          1          4 --.

Column 20,
Line 48, "tenn" should read -- term --.

Column 21,
Line 3, "polytirethanes" should read -- polyurethanes --.

Column 22,
Line 27, "polyurcthanc," should read -- polyurethane, --.
Table 17, column heading "*E. aerogens*" should read -- *E. aerogenes* --.

Column 23,
Line 5, "trypticasc" should read -- trypticase --.

Column 24,
Line 32, "inclubation" should read -- incubation --.
Line 37, "salicylatcs" should read -- salicylates --.
Table 19, "Salicylc Acid" should read -- Salicylic Acid --.

Column 26,
Lines 30-31, "polyvinylchlioride" should read -- polyvinylchloride --.

Column 27,
Line 3, "chlorhexidinie" should read -- chlorhexidine --.
Lines 33-34, "chliorhexidine" should read -- chlorhexidine --.

UNITED STATES PATENT AND TRADEMARK OFFICE
CERTIFICATE OF CORRECTION

PATENT NO. : 6,224,579 B1
DATED : May 1, 2001
INVENTOR(S) : Modak et al.

It is certified that error appears in the above-identified patent and that said Letters Patent is hereby corrected as shown below:

Column 28,
Line 19, "gramaciain" should read -- gramacidin --.

Signed and Sealed this

Twenty-seventh Day of July, 2004

JON W. DUDAS
*Acting Director of the United States Patent and Trademark Office*